United States Patent
Okajima et al.

(10) Patent No.: US 9,649,035 B2
(45) Date of Patent: May 16, 2017

(54) METHOD FOR DIAGNOSIS AND TREATMENT OF ARTERY

(71) Applicant: TERUMO KABUSHIKI KAISHA, Shibuya-ku (JP)

(72) Inventors: Naofumi Okajima, Chuo-ku (JP); Ryo Okamura, Fujinomiya (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 1030 days.

(21) Appl. No.: 13/866,415

(22) Filed: Apr. 19, 2013

(65) Prior Publication Data
US 2013/0281850 A1      Oct. 24, 2013

Related U.S. Application Data

(60) Provisional application No. 61/635,617, filed on Apr. 19, 2012.

(51) Int. Cl.
*A61B 5/02* (2006.01)
*A61B 17/3207* (2006.01)
(Continued)

(52) U.S. Cl.
CPC ...... *A61B 5/02007* (2013.01); *A61B 17/3207* (2013.01); *A61M 25/0102* (2013.01);
(Continued)

(58) Field of Classification Search
CPC .. A61M 25/00; A61M 25/01; A61M 25/0102; A61M 2025/0175; A61M 2025/0194; A61M 25/065; A61M 25/0662; A61M 2025/0681; A61B 5/02007; A61B 17/3207
See application file for complete search history.

(56) References Cited

U.S. PATENT DOCUMENTS 4,128,173 A * 12/1978 Lazarus ............. A61B 17/3415
                                                      206/362
5,062,285 A     11/1991 Groos
(Continued)

OTHER PUBLICATIONS

Hoffmann, K., Schott, U., Erb, M., Albes, J., Claussen, C. D., & Duda, S. H. (1998). Remote suturing for percutaneous closure of popliteal artery access. Catheterization and cardiovascular diagnosis, 43(4), 477-482.*

*Primary Examiner* — Bhisma Mehta
*Assistant Examiner* — Nilay Shah
(74) *Attorney, Agent, or Firm* — Buchanan, Ingersoll and Rooney PC

(57) ABSTRACT

An introducer having a dilator positioned in a sheath is inserted into a first artery and, thereafter, only the dilator tube is drawn out of the first artery and the sheath while the sheath remains in the first artery. A diagnostic instrument having an outer diameter smaller than a maximum outer diameter permitting insertion into the sheath tube is inserted into the second artery, and a stenosis of the second artery is diagnosed. While keeping the sheath indwelling in the first artery, a therapeutic instrument or a catheter permitting the therapeutic instrument to be inserted therein, which therapeutic instrument or catheter has a maximum outer diameter permitting insertion into the sheath tube, is inserted into the second artery, and the second artery is treated.

5 Claims, 6 Drawing Sheets

(51) Int. Cl.
A61M 25/01 (2006.01)
A61M 25/06 (2006.01)
A61M 29/00 (2006.01)

(52) U.S. Cl.
CPC ....... *A61M 25/065* (2013.01); *A61M 25/0662* (2013.01); *A61M 29/00* (2013.01); *A61M 2025/0681* (2013.01)

(56) References Cited

U.S. PATENT DOCUMENTS

| | | | | |
|---|---|---|---|---|
| 5,492,530 A | * | 2/1996 | Fischell ............ | A61M 25/0662 604/510 |
| 6,090,072 A | * | 7/2000 | Kratoska ............ | A61B 17/3439 604/164.01 |

* cited by examiner

FIG. 4
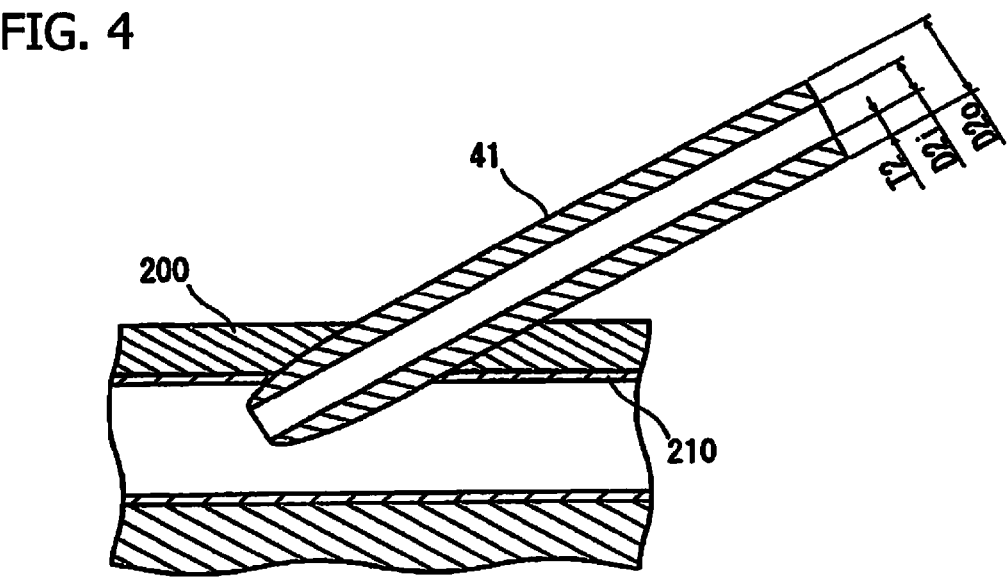
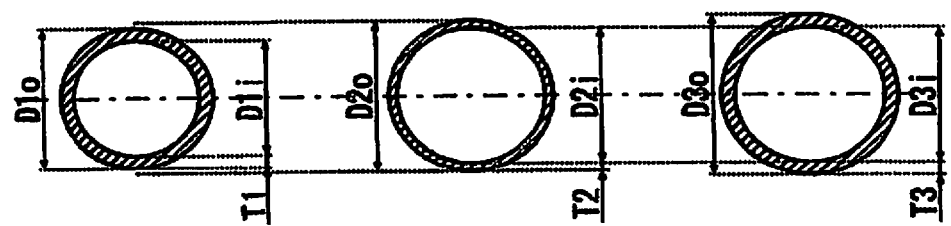
FIG. 5A    FIG. 5B    FIG. 5C

METHOD FOR DIAGNOSIS AND TREATMENT OF ARTERY

This application is based on and claims priority to U.S. Provisional Application No. 61/635,617 filed on Apr. 19, 2012, the entire content of which is incorporated herein by reference.

TECHNOLOGICAL FIELD

The present invention generally relates to a method for diagnosis and treatment of an artery.

BACKGROUND DISCUSSION

In medical care in recent years, medical treatments and tests in various forms have been conducted using thin, elongated, tubular medical instruments called catheters. As such therapeutic methods, procedures based on the use of a therapeutic catheter have been practiced utilizing the elongated nature of the catheter. Specific examples of such procedures include a method in which a medicine is administered directly to an affected part through a catheter, a method in which a stenosed (narrowed) part of a body lumen is forced open by use of a catheter equipped at its distal end with a balloon capable of being inflated by pressurization, a method in which a diseased part is cut away and opened by use of a catheter equipped with a cutter at a distal portion thereof, and a method in which, on the contrary, an aneurysm, a bleeding part or a nutrient vessel is closed by packing by use of a catheter. In addition, there is a therapeutic method in which a stent in the shape of a pipe with a meshed side surface is implanted and set indwelling in a body lumen by use of a catheter, for the purpose of keeping open a stenosed part of the body lumen. There are also cases where a thrombus obstructing a blood vessel is sucked away.

When conducting a treatment, test or the like by use of a catheter, in general, an introducer sheath is introduced into a puncture site in an arm or leg, by use of a catheter introducer, and a catheter or the like is percutaneously inserted into a lesion part of a blood vessel or the like through a lumen of the introducer sheath.

The introducer sheath is formed of a sheath tube, which is a tubular member having an inner cavity in which an elongated body such as a catheter can be inserted and passed. An example is U.S. Pat. No. 5,066,285. The introducer sheath has a distal portion which is located on the distal side at the time of introduction into a puncture part, and a main body section which is located on the proximal side of the distal portion.

In the case where a stenosis in an artery is found upon diagnosis of a patient's arteries and treatment is conducted in succession to the diagnosis, instead of conducting the treatment some other time, for example, the physical burden on the patient is heavy. In general, there is a tendency toward selection of a thinner diagnostic catheter in order to ensure lesser invasiveness and a tendency toward selection of a thicker therapeutic catheter and a thicker guiding catheter (for insertion of the therapeutic catheter) in order to permit appropriate execution of an intended procedure. In the case where a patient undergoes therapy following diagnosis, therefore, an introducer sheath having a small diameter used with a diagnostic catheter and having been inserted into the patient's artery has to be replaced by an introducer sheath having another size according for use with a therapeutic catheter. Set forth below is a description of a method for diagnosis and treatment of a coronary artery representing one example of the method for diagnosis and treatment of an artery.

Specifically, in a situation where a stenosis in a patient's artery is found upon diagnosis of the artery, it has been necessary to draw out an introducer sheath having been inserted in another artery or in another part of the same artery for introduction of a diagnostic catheter. After the drawing-out of the introducer sheath, it has been necessary to insert another introducer sheath with a larger inner diameter into the other artery or the other part of the same artery, for the purpose of introducing a therapeutic catheter into the patient's artery. For instance, in a situation where a stenosis in a patient's coronary artery is found upon diagnosis of the coronary artery, it has been necessary to draw out an introducer sheath which was previously inserted in the patient's radial artery or ulnar artery for introduction of a diagnostic catheter. After drawing-out the introducer sheath, it has been necessary to insert another introducer sheath with a larger inner diameter into the radial artery or ulnar artery, for the purpose of introducing a therapeutic catheter into the patient's coronary artery.

In this case, in the process of the patient undergoing diagnosis and treatment in succession, the two kinds of introducer sheaths differing in diameter are sequentially inserted into the patient's radial artery or ulnar artery. Such a procedure imposes a heavy physical burden on the patient.

SUMMARY

The method disclosed here for diagnosing and treating an artery makes it possible, when a stenosis is found upon diagnosis of a patient's artery and then treatment is conducted in succession to the diagnosis, instead of conducting the treatment some other time, for example, an introducer sheath already set indwelling in another artery or in another part of the same artery for introduction of a diagnostic catheter does not have to be replaced by another sheath having a larger inner diameter for insertion of a therapeutic catheter.

A method of treating a second artery of a patient by inserting a diagnostic instrument through a first artery into the second artery, diagnosing the second artery, thereafter inserting a therapeutic instrument through the first artery into the second artery of the patient, and treating the second artery, wherein the method comprise: preparing an introducer comprised of a dilator positioned inside a sheath, with the sheath possessing open distal and proximal ends, and the dilator possessing a distal end; inserting the introducer, in which the dilator is positioned inside the sheath with the distal end of the dilator positioned distally beyond the distal and of the sheath, into the first artery; removing the dilator from the sheath while keeping the sheath indwelled in the first artery; inserting the diagnostic instrument through the sheath that is indwelled in the first artery so that the diagnostic instrument is inserted into the first artery and then into the second artery, with the entirety of the diagnostic instrument that is inserted into the diagnostic instrument having an outer diameter smaller than the inner diameter of the sheath; and diagnosing through use of the diagnostic instrument positioned in the second artery that a stenosis exists in the second artery. The method further comprises removing the diagnostic instrument from the sheath and inserting the therapeutic instrument, or a catheter permitting insertion of the therapeutic instrument, through the sheath that is indwelled in the first artery so that the therapeutic instrument or catheter is inserted into the first artery and then into the second artery, with the entirety of the therapeutic instrument or catheter which is inserted into the sheath possessing a maximum outer diameter no greater than the inner diameter of the sheath, the maximum outer diameter of the portion of the therapeutic instrument or catheter which is inserted into the sheath being greater than the outer diameter of the entirety of the dilator that is inserted into the sheath, and when the catheter permitting insertion of the therapeutic instrument is inserted through the sheath and into the first and second arteries, the therapeutic instrument is inserted into the catheter and into the first and second arteries; and treating the stenosis in the second artery through use of the therapeutic instrument.

The inner diameter of the sheath into which the therapeutic instrument and the diagnostic instrument are inserted is 1.9 mm to 2.5 mm and the wall thickness of the sheath into which the therapeutic instrument and the diagnostic instrument are inserted is 0.05 to 0.19 mm. Alternatively, the inner diameter of the sheath into which the therapeutic instrument and the diagnostic instrument are inserted is 2.3 mm to 2.8 mm and the wall thickness of the sheath into which the therapeutic instrument and the diagnostic instrument are inserted is 0.05 to 0.19 mm. As a further alternative, the inner diameter of the sheath into which the therapeutic instrument and the diagnostic instrument are inserted is 2.0 mm to 2.4 mm and the wall thickness of the sheath into which the therapeutic instrument and the diagnostic instrument are inserted is 0.06 to 0.15 mm.

The first artery is preferably a radial artery or an ulnar artery, and the second artery is preferably a coronary artery.

The first artery is preferably a posterior tibial artery, a fibular artery, an anterior tibial artery, or a popliteal artery.

The sheath has a ratio of inner diameter to wall thickness in a range from 10 to 50, preferably from 13 to 40, more preferably from 15 to 30.

The diagnostic instrument is preferably an angiography catheter, an intravenous ultrasound testing instrument, or an intravenous optical coherence tomography instrument, and the therapeutic instrument is preferably a balloon catheter, a drug-eluting balloon catheter, a bare metal stent, a drug-eluting stent, a drug-eluting biodegradable stent, a rotablator, a thrombus suction catheter, or a drug administration catheter. The catheter can be a guiding catheter or a support catheter.

According to another aspect, a method of treating comprises: inserting an introducer into a first blood vessel, with the introducer comprising a dilator positioned inside a sheath which possesses open distal and proximal ends, and with the introducer being inserted into the blood vessel while the distal end of the dilator extends distally beyond the distal end of the sheath; drawing out the dilator from the first blood vessel and from the sheath while the sheath is kept indwelled in the first blood vessel; inserting a diagnostic instrument into the sheath that is indwelled in the first blood vessel, through the first blood vessel and into a second blood vessel, with the diagnostic instrument having an outer diameter inserted into the sheath that is smaller than a maximum outer diameter which can be inserted into and moved along the sheath; diagnosing, through use of the diagnostic instrument, whether a stenosis exists in the second blood vessel; and drawing out the diagnostic instrument from the second blood vessel, the first blood vessel and the sheath. The method additionally involves inserting the therapeutic instrument or a catheter permitting insertion of the therapeutic instrument, through the sheath that is indwelled in the first blood vessel so that the therapeutic instrument or catheter is inserted through the first blood vessel and then into the second blood vessel, with the therapeutic instrument or catheter having a maximum outer diameter which is permitted to be inserted into the sheath and moved along the sheath, and wherein the maximum outer diameter of the therapeutic instrument or catheter which is inserted into the sheath being greater than the outer diameter of the diagnostic instrument, and when the catheter permitting insertion of the therapeutic instrument is inserted through the sheath and the first blood vessel and into the second blood vessel, the therapeutic instrument is inserted through the catheter and the first blood vessel and into the second blood vessel. The stenosis in the second blood vessel is treated through use of the therapeutic instrument.

The first artery is preferably a radial artery or an ulnar artery, and the second artery is preferably a coronary artery. More specifically, the first artery is a posterior tibial artery, a fibular artery, an anterior tibial artery, or a popliteal artery.

The sheath can be configured to possess an inner diameter of 2.4 to 2.7 mm and a wall thickness of 0.06 to 0.15 mm, more specifically a wall thickness of 0.08 to 0.14 mm.

The sheath can be configured to have a ratio of inner diameter to wall thickness in a range from 12 to 56, preferably from 16 to 45, more preferably from 17 to 34.

The diagnostic instrument can be an angiography catheter, an intravenous ultrasound testing instrument, or an intravenous optical coherence tomography instrument, and the therapeutic instrument can be a balloon catheter, a drug-eluting balloon catheter, a bare metal stent, a drug-eluting stent, a drug-eluting biodegradable stent, a rotablator, a thrombus suction catheter, or a drug administration catheter. In addition, the catheter is preferably a guiding catheter or a support catheter.

The sheath can have an inner diameter of 1.6 to 2.0 mm and a wall thickness of 0.06 to 0.15 mm, more specifically a wall thickness of 0.08 to 0.14 mm.

The sheath can be can be figured to possess a ratio of inner diameter to wall thickness in a range from 7 to 42, preferably from 10 to 33, more preferably from 11 to 25.

The diagnostic instrument can be an angiography catheter, an intravenous ultrasound testing instrument, or an intravenous optical coherence tomography instrument.

According to another aspect, a method of inserting an angiography catheter and a guiding catheter through a first artery into a second artery of a patient comprises: preparing an introducer including a sheath and a dilator positioned in the sheath, with the sheath being provided as one of a plurality of different sheaths which have different inner diameters according to outer diameters of instruments sized to be inserted into and moved along inner cavities of the different sheaths of the sheath and each of which has an outer diameter substantially equal to an outer diameter of a first sheath and an inner diameter substantially equal to an inner diameter of a second sheath which is a size larger than the first sheath, and with the dilator possessing an outer diameter substantially equal to an inner diameter of the second sheath and insertable into and moved along the second sheath. The method also includes inserting the introducer into the first artery while the dilator is positioned in the sheath, removing the dilator from the sheath while the sheath remains indwelled in the first artery, inserting the angiography catheter through the sheath and the first artery and into the second artery, with the angiography catheter having an outer diameter equal to or smaller than a maximum outer diameter permitting insertion into and movement along the sheath, and diagnosing, through use of the angiography catheter, whether or not the second artery is stenosed. The method additionally involves removing the angiography catheter from the and second arteries and from the sheath, and inserting the guiding catheter, having the maximum outer diameter permitting insertion into the sheath, through the sheath and the first artery and into the second artery, without replacing the sheath with another sheath having a size larger than the inner diameter of the sheath.

When the introducer sheath is sized to have an inner diameter of 1.9 to 2.5 mm and a wall thickness of 0.05 to 0.19 mm is applied, the following effect is produced. That is, in the case where a stenosis is found upon diagnosis of a patient's second artery and treatment is conducted in succession, instead of conducting the treatment some other time, for example, the introducer sheath already set indwelling in a first artery does not have to be replaced by another one having a larger inner diameter for insertion of a therapeutic catheter. Here, the first artery is an artery in which to insert the introducer sheath, and the second artery is an artery to be diagnosed and treated (This terminology applies hereafter.). For instance, in the case where a stenosis is found upon diagnosis of a patient's coronary arteries and treatment is conducted in succession, instead of conducting the treatment at another time, for example, the introducer sheath already set indwelling in the radial artery or the ulnar artery does not have to be replaced by another one having a larger inner diameter for insertion of a therapeutic catheter.

Similarly, when the introducer sheath is sized to possess an inner diameter of 2.3 to 2.8 mm and a wall thickness of 0.05 to 0.19 mm, the following effect is produced. That is, in the case where a stenosis is found upon diagnosis of a patient's second artery and treatment is conducted in succession, instead of conducting the treatment at another time, for example, the introducer sheath already set indwelling in the first artery does not have to be drawn out of the first artery and inserted into another artery larger than the first artery in blood vessel diameter. For instance, in the case where a stenosis is found upon diagnosis of a patient's coronary arteries and treatment is conducted in succession, instead of conducting the treatment some other time, for example, the sheath already set indwelling in the radial artery or the ulnar artery does not have to be drawn out of the radial artery or the ulnar artery and inserted into a femoral artery or a brachial artery.

Similarly, when the introducer sheath is sized to have an inner diameter of 1.5 to 2.1 mm and a wall thickness of 0.05 to 0.19 mm, the following effect is produced. That is, in the case where a stenosis is found upon diagnosis of a patient's second artery and treatment is conducted in succession, instead of conducting the treatment some other time, for example, the introducer sheath already set indwelling in a first artery does not have to be replaced by another one having a larger inner diameter for insertion of a therapeutic catheter. For instance, in the case where a stenosis is found upon diagnosis of a patient's coronary arteries and treatment is conducted in succession, instead of conducting the treatment at some other time, for example, the introducer sheath already set indwelling in the radial artery or the ulnar artery does not have to be replaced by another one having a larger inner diameter for insertion of a therapeutic catheter.

Similarly, when the introducer sheath is sized to possess an inner diameter of 1.1 to 1.7 mm and a wall thickness of 0.05 to 0.19 mm, the following effect is produced. That is, in the case where a stenosis is found upon diagnosis of a patient's second artery and treatment is conducted in succession, instead of conducting the treatment at some other time, for example, the introducer sheath already set indwelling in a first artery does not have to be replaced by another one having a larger inner diameter for insertion of a therapeutic catheter. For instance, in the case where a stenosis is found upon diagnosis of a patient's coronary arteries and treatment is conducted in succession, instead of conducting the treatment some other time, for example, the introducer sheath already set indwelling in the radial artery or the ulnar artery does not have to be replaced by another one having a larger inner diameter for insertion of a therapeutic catheter.

In addition, of the introducer sheaths as above-mentioned, those which are small in inner diameter are preferable for use in the case where the introducer sheath is introduced into an artery having a small blood vessel diameter. Examples of such a case include cases where the introducer sheath is introduced through the instep or the heel to be set indwelling in a posterior tibial artery, a fibular artery, or an anterior tibial artery.

BRIEF DESCRIPTION OF THE DRAWING FIGURES

FIG. 4 is a schematic view illustrating a condition where the introducer sheath is set indwelling in a blood vessel.

FIGS. 5A to 5C are cross-sectional views, taken in a normal direction relative to an axial direction, illustrating sizes of three kinds of introducer sheaths.

DETAILED DESCRIPTION

Figure 1:
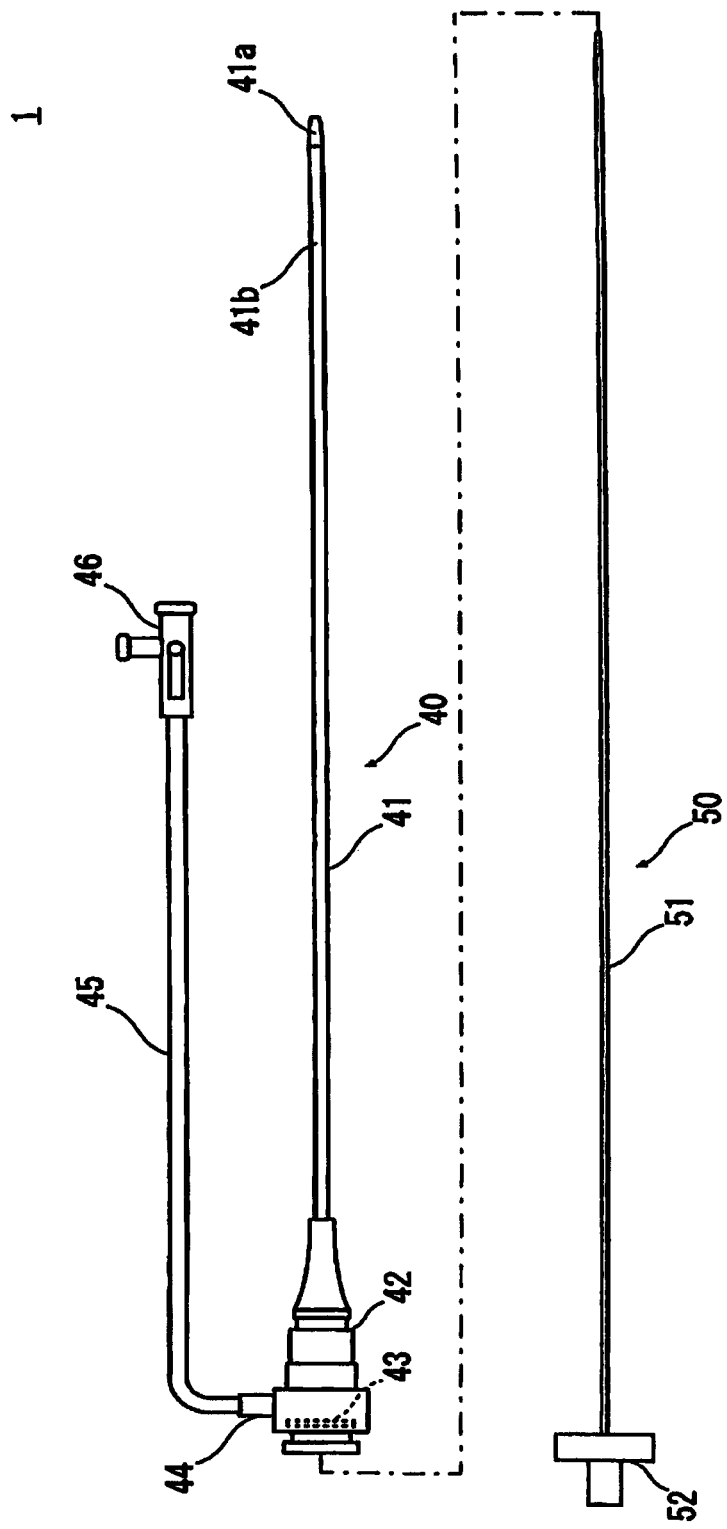
FIG. 1 is a plan view of an introducer assembly based on the application of an introducer sheath according to one embodiment disclosed here by way of example.

An embodiment of the method disclosed here will be described below, referring to the accompanying drawings. In the following description, common features are identified by common reference numerals and a detailed description of features previously described will not be repeated. Dimensional ratios in the drawings are exaggerated for convenience of description, illustration and understanding, and may be different from actual dimensional ratios.

A configuration of an introducer assembly 1 based on the application of an introducer sheath 40 according one embodiment disclosed here as an example will be described referring to FIG. 1

As shown in FIG. 1, the introducer assembly 1 includes the introducer sheath 40 for securing an access route to the inner of a body lumen, and a dilator 50 for assisting the insertion of the introducer sheath 40 that is to be percutaneously indwelled in the body lumen.

The introducer sheath 40 includes a sheath having open distal and proximal ends. More specifically, the introducer sheath 40 includes, for example, a sheath tube 41 having open distal and proximal ends, a sheath hub 42, a hemostasis valve 43, a side port 44, a tube 45, and a three-way cock 46. The sheath tube 41 is percutaneously put indwelling (indwelled) in a body lumen, after which an angiography catheter, serving as an example of a diagnostic instrument, or a balloon, a stent or the like, serving as an example of a therapeutic instrument, is inserted into and moved along the sheath tube 41, to be thereby introduced into the body lumen. The sheath hub 42 permits the sheath tube 41 and the side port 44 to communicate with each other interiorly of the sheath tube 41 and the side port 44. The hemostasis valve 43 is incorporated in the sheath hub 42. The hemostasis valve 43 stanches (stops) blood flowing out of a blood vessel through the sheath tube 41. The side port 44 permits communication between the sheath tube 41 and the tube 45. The tube 45 permits communication between the side port 44 and the three-way cock 46. The three-way cock 46 is used to inject a liquid such as physiological saline into the introducer sheath 40 through the tube 45 and the side port 44.

Examples of the material forming the sheath 40 include polyethylene, polyethylene terephthalate, polypropylene, polyamides, polyamide elastomers, polyimides, polyurethane, PEEK (polyether ether ketone), and fluorine-based polymer such as ETFE, PFA, or FEP, among which ETFE and PEEK are preferred in consideration of an anti-kinking effect which will be described later.

The dilator 50 includes, for example, a dilator tube 51 and a dilator hub 52. The dilator tube 51 of the dilator 50 is inserted into and moved along the sheath tube 41 so the distal end of the dilator is positioned distally beyond the distal and of the sheath. The dilator tube 51 (dilator) assists the insertion of the introducer sheath 40 which is to be percutaneously indwelled in a body lumen. The dilator hub 52 holds the dilator tube 51 in the state of being detachably attachable to the sheath hub 42. The outer diameter of the dilator tube 51 is substantially equal to or slightly smaller than the inner diameter of the sheath tube 41.

Figure 2:
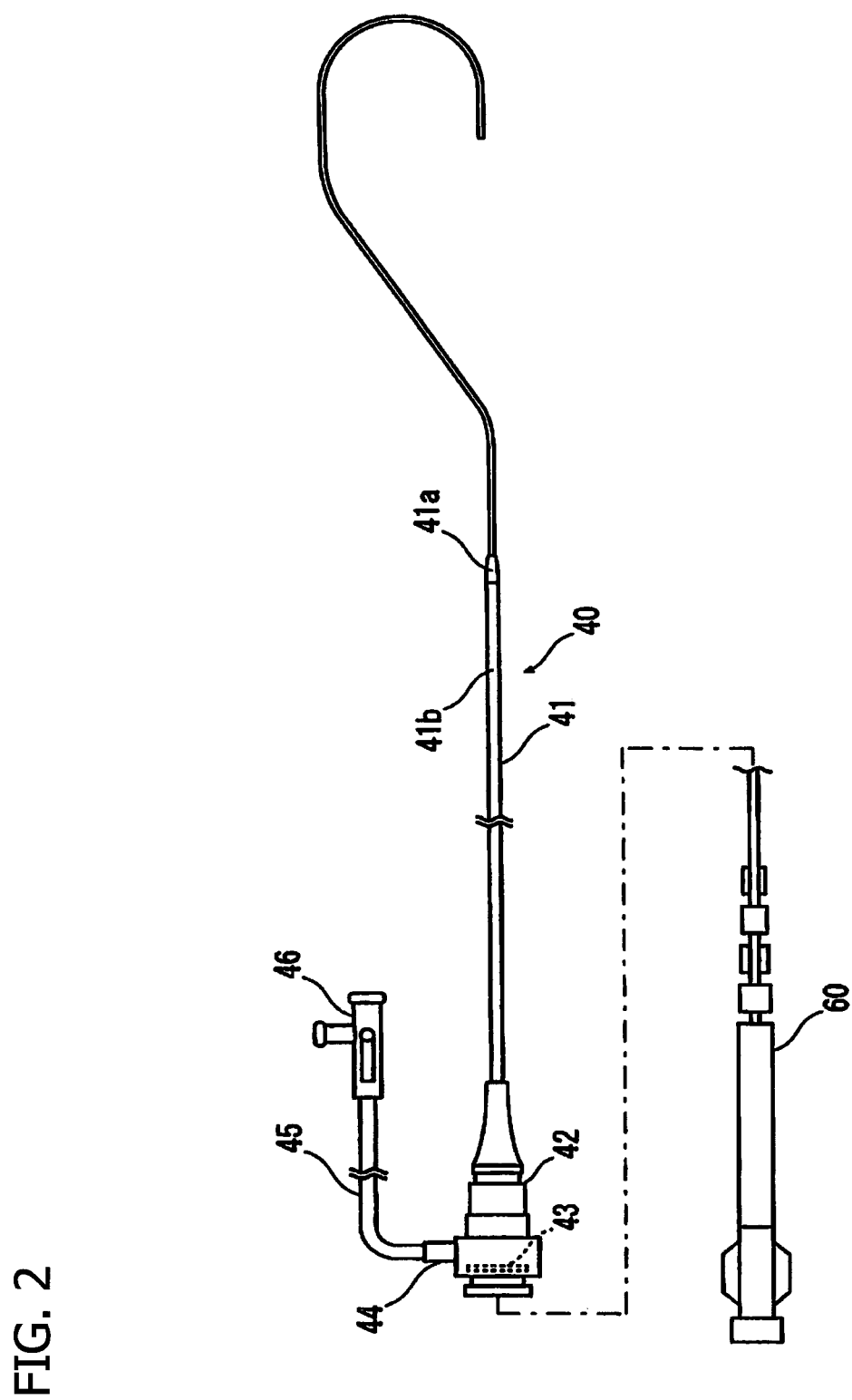
FIG. 2 is a plan view showing a condition in which a diagnostic instrument or a therapeutic instrument is inserted in the introducer sheath.

Set forth next, with reference to FIG. 2, is a description of a configuration or assembly in which a diagnostic instrument or a therapeutic instrument is inserted in the introducer sheath 40 according to this embodiment.

FIG. 2 illustrates the condition in which an instrument 60 composed of a diagnostic instrument or a therapeutic instrument is inserted in the introducer sheath 40.

The instrument 60 is inserted into the introducer sheath 40 after the introducer sheath 40 is inserted in a blood vessel and after the dilator 50 is drawn out of the introducer sheath 40. The instrument 60 has an elongated body, and is inserted into the blood vessel through the introducer sheath 40. In the case of the instrument 60 being a diagnostic instrument, examples of the instrument 60 include an angiography catheter, an intravascular ultrasound testing instrument, or an intravascular optical coherence tomography instrument. In the case of the instrument 60 being a therapeutic instrument, examples of the instrument 60 include a balloon catheter, a drug-eluting balloon catheter, a bare metal stent, a drug-eluting stent, a drug-eluting biodegradable stent, a rotablator, a thrombus suction catheter, or a drug administration catheter.

A procedure for percutaneously inserting the introducer sheath 40 of this embodiment into a blood vessel will be specifically described below, referring to FIGS. 3A to 3H.

FIGS. 3A to 3H are schematic views illustrating, in the order from 3A to 3H, the procedure of percutaneously inserting the introducer sheath 40 into a blood vessel.

Figure 3A:
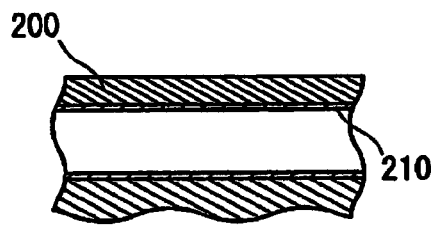
FIGS. 3A to 3H are schematic views illustrating, in the order of 3A to 3H, a procedure of percutaneously inserting the introducer sheath into a blood vessel.
Figure 3E:
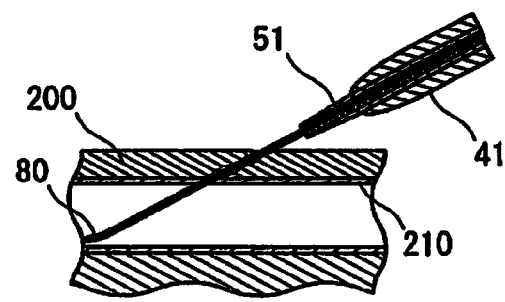
Figure 3B:
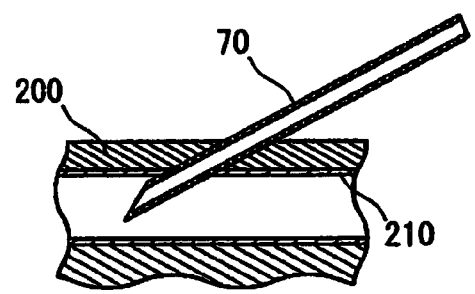
Figure 3F:
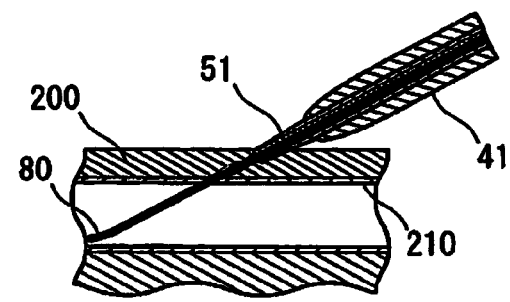
Figure 3C:
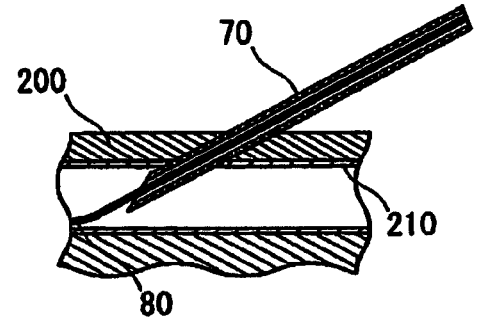
Figure 3G:
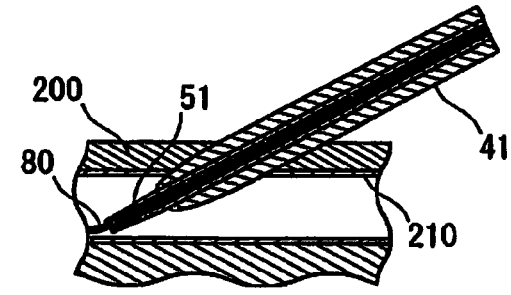
Figure 3D:
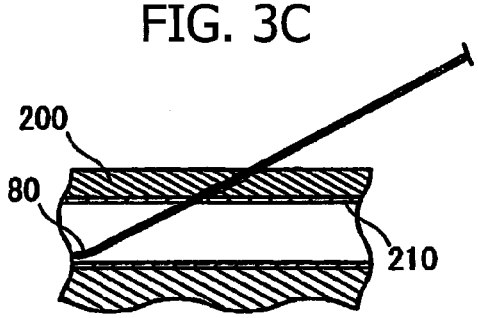
Figure 3H:
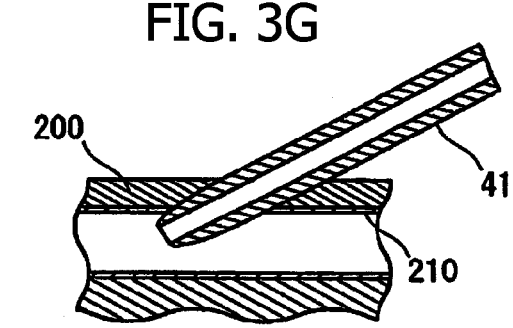

The sheath tube 41 of the introducer sheath 40 is inserted through skin 200, shown in FIG. 3A, into a blood vessel 210 located beneath the skin 200. Specifically, first, as shown in FIG. 3B, a puncture needle 70 punctures the skin 200 toward the blood vessel 210. Next, as shown in FIG. 3C, a guide wire 80 is inserted through the lumen of the puncture needle 70 into the blood vessel 210. Subsequently, as shown in FIG. 3D, the puncture needle 70 is drawn out of (removed from) the blood vessel 210, with the guide wire 80 kept indwelling in the blood vessel 210. Next, as shown successively in FIG. 3E to FIG. 3G, the dilator tube 51 together with the sheath tube 41 (i.e., the dilator 51 positioned in the sheath tube 41) is inserted into the blood vessel 210 along the guide wire 80 and through the skin 200. Subsequently, as shown in FIG. 3H, the guide wire 80 and the dilator tube 51 are drawn out of the blood vessel 210, with the sheath tube 41 kept indwelling in the blood vessel 210. Thereafter, the diagnostic instrument or therapeutic instrument is inserted into the sheath tube 41.

The shape of the introducer sheath 40 according to this embodiment will be specifically described below, with reference to FIGS. 4 and 5A to 5C.

FIG. 4 schematically illustrates a condition where the introducer sheath is indwelled in the blood vessel, while FIGS. 5A to 5C illustrate cross-sectional sizes of three kinds of introducer sheaths.

As shown in FIG. 4, the outer diameter $D2o$ of the introducer sheath 40 is preferably set as small as possible, for helping to ensure relatively easy puncturing of the skin and a blood vessel, and for reducing invasiveness to vascular endothelium. In addition, the outer diameter $D2o$ of the introducer sheath 40 is preferably set as small as possible, for accelerating the recovery of a punctured part after the treatment and for shortening the stanching time. On the other hand, the inner diameter $D2i$ of the introducer sheath 40 is preferably set as large as possible, for permitting insertion of elongated bodies possessing large outer diameters.

FIG. 5B shows a cross-sectional shape/size of the introducer sheath according to this embodiment, and FIGS. 5A and 5C show cross-sectional shapes/sizes of introducer sheaths according to known constructions. Here, FIG. 5B shows the outer diameter $D2o$, the inner diameter $D2i$ and the wall thickness $T2$ of the introducer sheath 40 according to this embodiment. FIG. 5A shows the outer diameter $D1o$, the inner diameter $D1i$ and the wall thickness $T1$ of an introducer sheath according to a known construction. The known configuration of the introducer sheath shown in FIG. 5A is smaller in inner diameter than the introducer sheath 40 of this embodiment. However, both the outer diameter of the introducer sheath shown in FIG. 5A and the outer diameter of the introducer sheath 40 of this embodiment have almost the same size. FIG. 5C shows the outer diameter $D3o$, the inner diameter $D3i$ and the wall thickness $T3$ of an introducer sheath according to another known construction. This known construction or configuration possesses a greater outer diameter than the introducer sheath 40 of this embodiment. And this known construction or configuration possesses an inner diameter substantially equal to the introducer sheath 40 of this embodiment.

The outer diameter $D2o$ of the introducer sheath 40 shown in FIG. 5B has an outer diameter which is smaller than the outer diameter $D3o$ and closer to the diameter $D1o$ than $D3o$. In other words, the known introducer sheath shown in FIG. 5A corresponds to 5 Fr size. The phrase "an introducer sheath corresponding to 5 Fr size" means that the inner diameter of the introducer sheath can be inserted a device having an outer diameter of 5 Fr size. The outer diameter $D2o$ of the introducer sheath 40 shown in FIG. 5B is equivalent to the outer diameter of 5 Fr size introducer sheath. For instance, the terms "a device" of the preceding sentence means a diagnostic instrument or a therapeutic instrument.

The inner diameter D2$i$ of the introducer sheath 40 shown in FIG. 5B has been enlarged to be comparable to the inner diameter D3$i$ of the known introducer sheath shown in FIG. 5C that is larger than the introducer sheath 40 by, for example, 1 Fr size. The conventional introducer sheath shown in FIG. 5C corresponds to 6 Fr size. Therefore, the introducer sheath shown in FIG. 5B can be concluded to correspond to 6 Fr size.

Furthermore, the wall thickness T2 of the introducer sheath 40 shown in FIG. 5B is configured to be smaller than the wall thickness T1 of the known introducer sheath shown in FIG. 5A and also smaller than the wall thickness T3 of the known introducer sheath shown in FIG. 5C. Thus, the introducer sheath 40 shown in FIG. 5B has the outer diameter D2$o$ reduced by 1 Fr size and the wall thickness T2 reduced, as compared with those according to the related art, whereby the introducer sheath 40 possesses the inner diameter D2$i$ which is enlarged by 1 Fr size. In other words, the introducer sheath 40 shown in FIG. 5B has the inner diameter D2$i$ that can be inserted a device having an outer diameter of 6 Fr size. When the inner diameter D2$i$ is larger than 6 Fr size, the inner diameter D2$i$ is 0.1 mm-0.3 mm larger than 6 Fr size (i.e., 0.2 mm). Also, the introducer sheath 40 shown in FIG. 5B has the outer diameter D2$o$. The outer diameter D2$o$ is close to the outer diameter D1$o$ of the known introducer sheath that corresponds to 5 Fr size. The wall thickness T2 of the introducer sheath 40 may be formed to be smaller than both the wall thickness T1 and the wall thickness T3.

Specifically, the prior art introducer sheath shown in FIG. 5A can have inserted therein a device having an outer diameter of 5 Fr size. Thus, the introducer sheath in FIG. 5A means that the inner diameter D1$i$ is 5 Fr size or is larger than 5 Fr size. In addition, the outer diameter of the introducer sheath shown in FIG. 5A is larger than 5 Fr size by a wall thickness of the introducer sheath shown in FIG. 5A. For example, the wall thickness T1 of the introducer sheath shown in FIG. 5A is 0.2 mm. In this case, the outer diameter D1$o$ of the introducer sheath shown in FIG. 5A is 2.6 mm. Also, the prior art introducer sheath shown in FIG. 5B and FIG. 5C can have inserted therein a device having an outer diameter of 6 Fr size. Thus, the introducer sheath in FIGS. 5B and 5C means that the inner diameter D2$i$ and D3$i$ are larger than 6 Fr size. In addition, the outer diameter D3$o$ of the prior art introducer sheath shown in FIG. 5C is larger than 6 Fr size by a wall thickness of the introducer sheath shown in FIG. 5C. For example, the wall thickness T3 of the introducer sheath shown in FIG. 5C is 0.2 mm. In this case, the outer diameter D3$o$ of the introducer sheath shown in FIG. 5C is 3.0 mm. But, the introducer sheath 40 shown in FIG. 5B of this embodiment has the inner diameter D2$o$ that can have inserted therein a device having an outer diameter of 6 Fr size and the outer diameter D2$o$ of the introducer sheath 40 shown in FIG. 5B of this embodiment is smaller by approximately 1 Fr (⅓ mm) than the outer diameter D3$o$ of the introducer sheath shown in FIG. 5C. In other words, the outer diameter D2$o$ of the introducer sheath shown in FIG. 5B approaches the outer diameter D1$o$ of the introducer sheath shown in FIG. 5A. Thus, the introducer sheath 40 is reduced in wall thickness T2, whereby it is reduced in outer diameter D2$o$ by 1 Fr size, without reducing the inner diameter D2$i$. Accordingly, the introducer sheath 40 ensures that a device with an outer diameter corresponding to 6 Fr size can be inserted into and moved along the sheath having an outer diameter D2$o$ almost corresponding to an outer diameter D1$o$ of the introducer sheath shown in FIG. 5A that can have inserted therein a device having an outer diameter of 5 Fr size.

Such an introducer sheath 40 is expressed as "6 in 5" in this application. This is because the inner diameter can have inserted therein a device having an outer diameter of 6 Fr size and the outer diameter is equivalent to an outer diameter of a prior art introducer sheath corresponding to 5 Fr size. Similarly, the introducer sheath 40 ensures that a device with an outer diameter corresponding to 7 Fr size can be inserted into and moved along the sheath having an outer diameter D2$o$ almost corresponding to an outer diameter D1$o$ of the introducer sheath shown in FIG. 5A that can be inserted into a device having outer diameter of 6 Fr size. Such an introducer sheath 40 is expressed as "7 in 6" in this application. This is because the inner diameter can have inserted therein a device having an outer diameter of 7 Fr size and the outer diameter is equivalent to an outer diameter of a prior art introducer sheath corresponds to 6 Fr size. Similarly, the introducer sheath 40 ensures that a device with an outer diameter corresponding to 5 Fr size can be inserted into and moved along the sheath having an outer diameter D2$o$ almost corresponding to an outer diameter D1$o$ of the introducer sheath shown in FIG. 5A that can be inserted into a device having an outer diameter of 4 Fr size. Such an introducer sheath 40 is expressed as "5 in 4" in this application. This is because the inner diameter can have inserted therein a device having an outer diameter of 5 Fr size and the outer diameter is equivalent to an outer diameter of a prior art introducer sheath corresponds to 4 Fr size. Similarly, the introducer sheath 40 ensures that a device with an outer diameter corresponding to 4 Fr size can be inserted into and moved along the sheath having an outer diameter D2$o$ almost corresponding to an outer diameter D1$o$ of the introducer sheath shown in FIG. 5A that can be inserted into a device having an outer diameter of 3 Fr size. Such an introducer sheath 40 is expressed as "4 in 3" in this application. This is because the inner diameter can be have inserted therein a device having an outer diameter of 4 Fr size and the outer diameter is equivalent to an outer diameter of a prior art introducer sheath corresponds to 3 Fr size.

A procedure for diagnosis or treatment of a coronary artery 320 by use of a diagnostic instrument or a therapeutic instrument through the introducer sheath 40 according to this embodiment will now be described with reference to FIG. 6.

Figure 6:
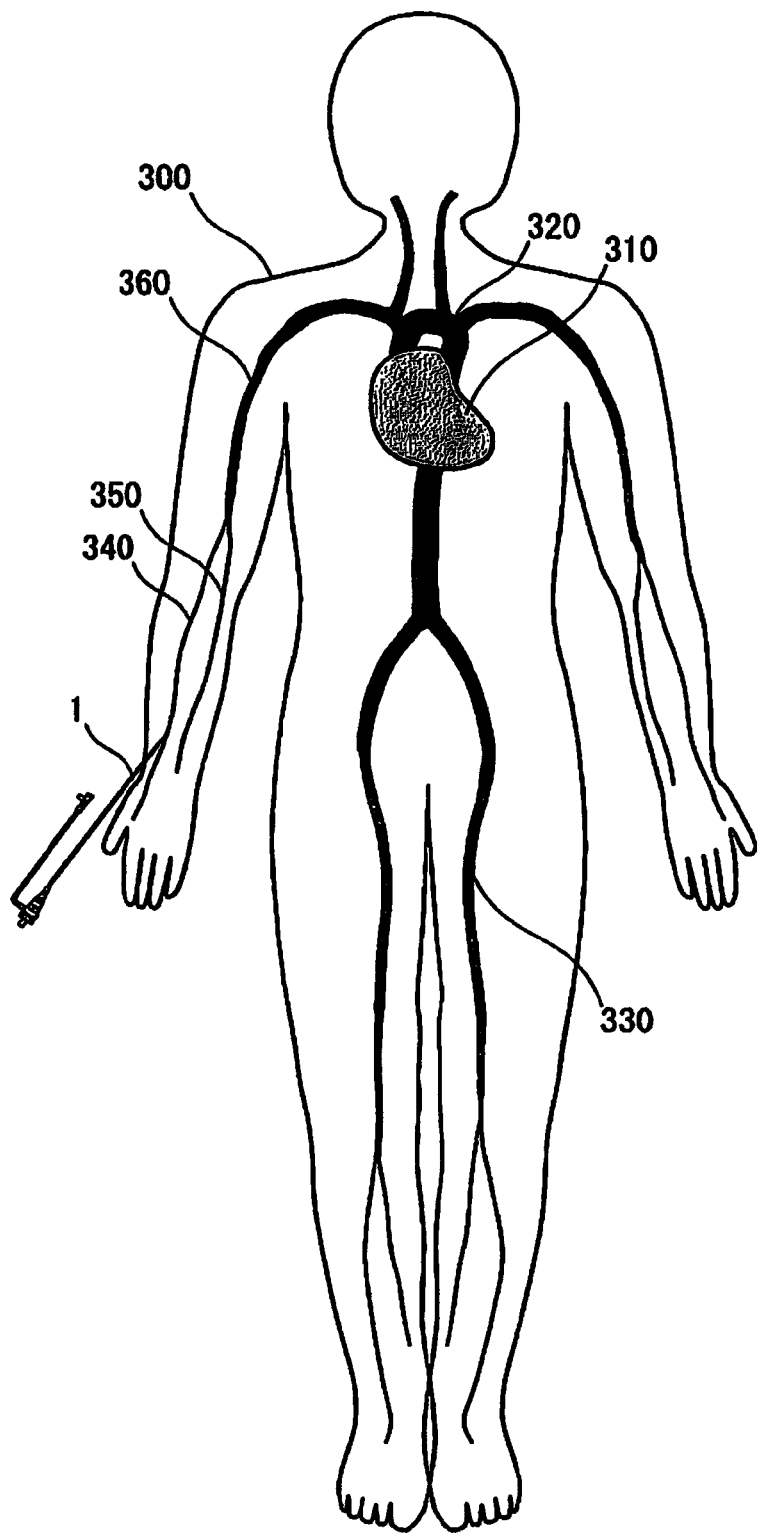
FIG. 6 is a schematic illustration of a condition where the introducer sheath is inserted into a predetermined blood vessel of a patient.

FIG. 6 schematically illustrates a condition in which the introducer sheath 40 is inserted in a predetermined blood vessel of a patient 300.

In a case where diagnosis of the coronary artery 320 of the patient 300 is conducted by inserting a diagnostic instrument through a radial artery 340 or ulnar artery 350 into the coronary artery 320 of the patient 300 and thereafter treatment of the coronary artery 320 is conducted by inserting a therapeutic instrument through the radial artery 340 or ulnar artery 350 into the coronary artery 320, the procedure is carried out as follows.

First, an introducer having the dilator 50 inserted into and extending along the introducer sheath 40 is inserted into the radial artery 340, and then the dilator 50 is drawn out, with the introducer sheath 40 kept indwelling in the radial artery 340. It is also possible for the introducer to be inserted into the ulnar artery 350. Next, a diagnostic instrument having an outer diameter smaller than the maximum outer diameter permitted to be inserted into the introducer sheath 40 is inserted into the introducer sheath 40 and is inserted through the radial artery 340 into the coronary artery 320. A diagnosis is then made through the diagnostic instrument whether or not the coronary artery 320 is stenosed, and the diagnostic instrument is then drawn out. Further, when the coronary artery 320 is found stenosed, the introducer sheath 40 is kept indwelling in the radial artery 340, then, in this condition, a therapeutic instrument or a catheter permitting the therapeutic instrument to be inserted therein, which therapeutic instrument or catheter has the maximum outer diameter permitting insertion into the introducer sheath, is inserted into the introducer sheath 40, is inserted through the radial artery 340 into the coronary artery 320. When a catheter permitting insertion of the therapeutic instrument is inserted into the sheath, the therapeutic instrument is inserted into the catheter. Treatment is then performed. The diagnostic instrument having an outer diameter smaller than the maximum outer diameter permitting insertion into the introducer sheath 40 has an outer diameter smaller than the maximum outer diameter by, for example, 1 Fr size.

Figure 7:
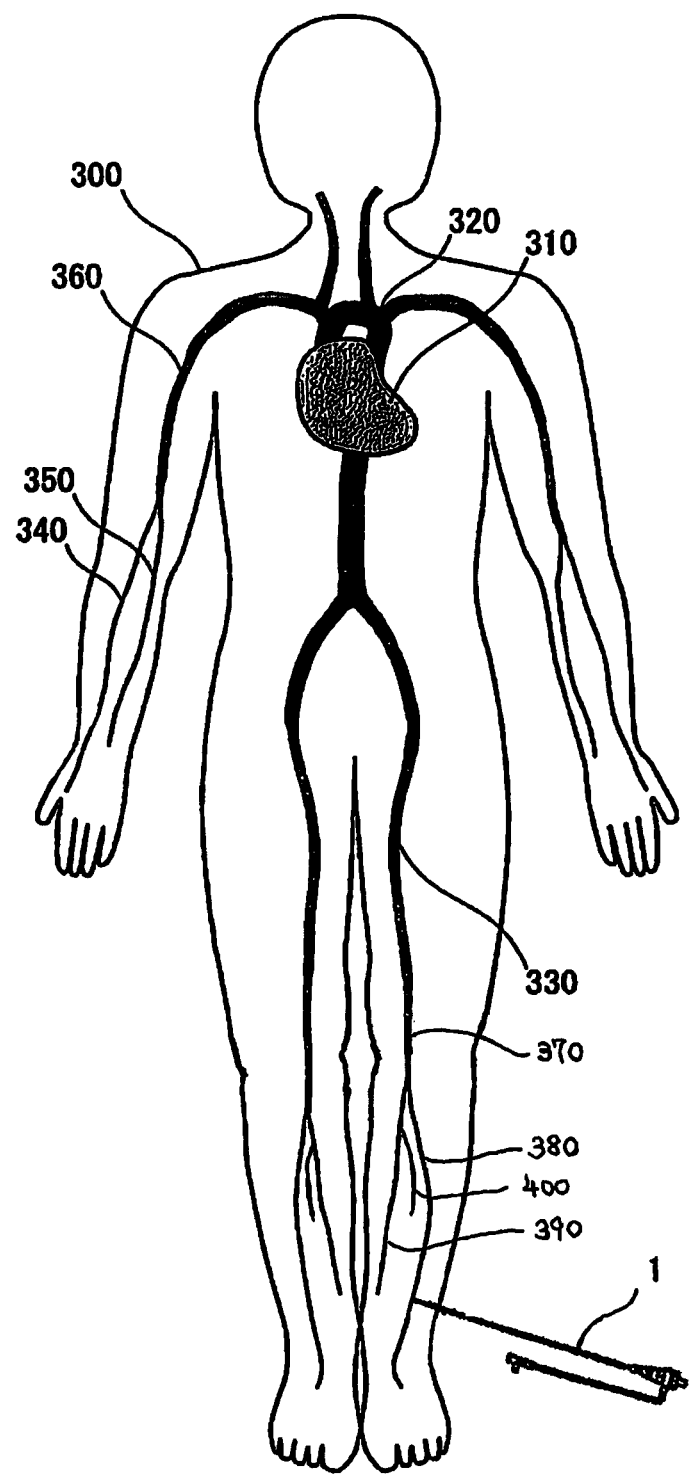
FIG. 7 is a schematic illustration of another way in which the introducer sheath is inserted into a predetermined blood vessel of a patient.

FIG. 7 schematically illustrates another condition where the introducer sheath 40 is inserted in a predetermined blood vessel of the patient 300.

In the case where the introducer sheath is introduced through a part near the back of the knee, the instep, or the heel to be set indwelling in a posterior tibial artery 390, a fibular artery 400, an anterior tibial artery 380, or a popliteal artery 370, as shown in FIG. 7, a procedure the same as or similar to the above-mentioned procedure shown in FIG. 6 is used. Specifically, a diagnostic instrument is inserted through the posterior tibial artery 390, the fibular artery 400, the anterior tibial artery 380, or the popliteal artery 370 of the patient 300 into an artery that is the part to be treated, and the artery to be treated is diagnosed. Thereafter, a therapeutic instrument is inserted through the patient's posterior tibial artery 390, fibular artery 400, anterior tibial artery 380, or popliteal artery 370 into the artery to be treated. Then, the artery as the part to be treated can be treated.

This embodiment of the diagnostic/treatment method permits realization of a variety of effects.

In the case where diagnosis of a second artery of the patient 300 is conducted by inserting a diagnostic instrument through a first artery into the second artery and then treatment of the second artery of the patient 300 is conducted by inserting a therapeutic instrument through the first artery into the second artery, various effects are produced according to the size of the introducer sheath 40. For instance, in the case where the diagnosis of the coronary artery 320 of the patient 300 is conducted by inserting the diagnostic instrument through the patient's radial artery 340 or ulnar artery 350 into the coronary artery 320 and subsequently the treatment of the coronary artery 320 is conducted by inserting the therapeutic instrument through the patient's radial artery 340 or ulnar artery 350 into the coronary artery 320, various effects are produced according to the size of the introducer sheath 40. In view of this, sizes of two kinds of introducer sheaths 40 will be specifically described.

In the case of an introducer sheath 40 having an inner diameter of 1.9 to 2.5 mm and a wall thickness of 0.05 to 0.19 mm, corresponding to the "6 in 5" mentioned above, the following effects are produced.

In a case where a stenosis is found upon diagnosis of the coronary artery 320 of a heart 310 of the patient 300 and treatment is conducted in succession to (following) the diagnosis, instead of conducting the treatment some other time, for example, the introducer sheath 40 already set indwelling in the radial artery 340 or ulnar artery 350 does not have to be replaced by another one with a larger inner diameter.

In the case of conducting treatment in succession to diagnosis, in the previously used procedures, a sheath in which to insert and pass a device corresponding to 5 Fr size has had to be replaced by a sheath in which to insert and pass a therapeutic device corresponding to 6 Fr size. Such replacement of the sheath in the previously used procedures has produced various problems. The replacement of the sheath in the previously used procedures causes re-insertion of the sheath, leading to increased invasiveness to the patient 300 and a need for a sheath-replacing time. In addition, two sheaths are necessitated, which leads to increased cost.

The sheath 40 corresponding to the "6 in 5" described above, when having an inner diameter of 2.0 to 2.4 mm and a wall thickness of 0.06 to 0.15 mm, helps ensure low invasiveness to the patient 300. The sheath 40, with the above-mentioned inner diameter and wall thickness, permits insertion therein of therapeutic catheters and guiding catheters with larger outer diameters. Where the sheath 40 has a wall thickness of 0.08 to 0.14 mm, the above-mentioned effects become even more noticeable.

The ratio of inner diameter to wall thickness, or (inner diameter)/(wall thickness), of the sheath 40 is in a range from 10 to 50, preferably from 13 to 40, more preferably from 15 to 30.

In a case of an introducer sheath 40 having an inner diameter of 2.3 to 2.8 mm and a wall thickness of 0.05 to 0.19 mm, corresponding to the "7 in 6" mentioned above, the following effects are produced.

In the case where a stenosis is found upon diagnosis of the coronary artery 320 of the heart 310 of the patient 300 and thereafter treatment is conducted in succession to (following) the diagnosis, instead of conducting the treatment some other time, for example, the sheath already set indwelling (indwelled) in the radial artery 340 or ulnar artery 350 does not have to be drawn out of the radial artery 340 or ulnar artery 350 and inserted into a brachial artery 360 or femoral artery 330.

In the case of conducting treatment in succession to diagnosis, in the previously used procedures, a TRI (Trans Radial Intervention) procedure could not be performed using such a device as a catheter of 7 Fr size which can cope with a difficult case, since the outer diameter (7 Fr size) of the sheath in which to insert and pass a device of 7 Fr size is larger than the blood vessel diameter (about 2.9±0.6 mm) of the radial artery 340 or ulnar artery 350. The TRI procedure is a procedure in which an introducer sheath is introduced through a radial artery 340 or ulnar artery 350 of an arm. This procedure is relatively low in invasiveness, and therefore imposes a relatively low burden on the patient. In addition, the procedure ensures easy hemostasis, a short stanching time, and earlier discharge of the patient from the hospital, which has a high medical economic effect on the hospital. Conventionally, however, the TRI procedure with these various merits has been abandoned due to the limitations on the size of the devices which can be inserted in the procedure, and a TFI procedure has been adopted. The TFI (Trans Femoral Intervention) procedure is a procedure in which an introducer sheath is introduced through a femoral artery 330 of a leg. As compared with the TRI procedure, the TFI procedure involves more difficult hemostasis at the punctured part, and the patient 300 needs a longer rest period after the treatment, and cannot be said to be comparable in the risk of the patient 300 suffering a hemorrhagic complication. That is, the TFI procedure has a greater risk of hemorrhagic complication than TRI.

The sheath 40 corresponding to the "7 in 6" mentioned above, when having an inner diameter of 2.4 to 2.7 mm and a wall thickness of 0.06 to 0.15 mm, helps ensures low invasiveness to the patient 300. The sheath 40, with the above-mentioned inner diameter and wall thickness, is configured to permit the insertion therein of therapeutic catheters and guiding catheters with larger outer diameters. Where the sheath 40 has a wall thickness of 0.08 to 0.14 mm, the above-mentioned effects become even more apparent.

The sheath 40 has the ratio of inner diameter to wall thickness in a range from 12 to 56, preferably from 16 to 45, more preferably from 17 to 34.

In addition, aside from the sizes of the above-mentioned two kinds of introducer sheaths 40, the introducer sheath 40 so shaped as to have an inner diameter of 1.5 to 2.1 mm and a wall thickness of 0.05 to 0.19 mm, which corresponds to the "5 in 4" described above, produces the same or similar effect to that of the introducer sheath 40 corresponding to the "6 in 5," as follows. For instance, in the case where a stenosis is found upon diagnosis of the coronary artery 320 of the heart 310 of the patient 300 and then treatment is conducted in succession, instead of conducting the treatment some other time, the sheath already set indwelling in the radial artery 340 or the ulnar artery 350 does not have to be replaced by another one having a larger inner diameter. In the case of conducting treatment in succession to (following) diagnosis, in the previously used procedures, a sheath in which to insert a device corresponding to 4 Fr size has had to be replaced by a sheath in which to insert a therapeutic device corresponding to 5 Fr size. Such replacement of the sheath in the related art has produced various problems. The replacement of the sheath in the previously used procedures requires re-insertion of the sheath, leading to increased invasiveness to the patient 300 and a need for a sheath-replacing time. In addition, two sheaths are necessitated, which leads to increased cost. The sheath 40 corresponding to "5 in 4" described above, when having an inner diameter of 1.5 to 2.1 mm and a wall thickness of 0.06 to 0.15 mm, helps ensure low invasiveness to the patient 300. The sheath 40, with the above-mentioned inner diameter and wall thickness, permits insertion therein of therapeutic catheters and guiding catheters with larger outer diameters. Where the sheath 40 has a wall thickness of 0.08 to 0.14 mm, the above-mentioned effects become even more pronounced. The ratio of inner diameter to wall thickness, or (inner diameter)/(wall thickness), of the sheath 40 is in a range from 7 to 42, preferably from 10 to 33, more preferably from 11 to 25.

Similarly, the introducer sheath 40 so sized as to have an inner diameter of 1.1 to 1.7 mm and a wall thickness of 0.05 to 0.19 mm, which corresponds to the "4 in 3" described above, produces the same or similar effect to that of the introducer sheath 40 corresponding to the "6 in 5," as follows. For example, in the case where a stenosis is found upon diagnosis of the coronary artery 320 of the heart 310 of the patient 300 and then treatment is conducted in succession, instead of conducting the treatment some other time, the sheath already set indwelling in the radial artery 340 or the ulnar artery 350 does not have to be replaced by another one having a larger inner diameter. In the case of conducting treatment in succession to (following) diagnosis, in the previously used procedures, a sheath in which to insert a device corresponding to 4 Fr size has had to be replaced by a sheath in which to insert a therapeutic device corresponding to 5 Fr size. Such replacement of the sheath in the previously used procedures has produced various problems. The replacement of the sheath in the previously used procedures causes re-insertion of the sheath, leading to increased invasiveness to the patient 300 and a need for sheath-replacing time. In addition, two sheaths are needed, which leads to a rise in cost. The sheath 40 corresponding to "4 in 3" described above, when having an inner diameter of 1.1 to 1.7 mm and a wall thickness of 0.06 to 0.15 mm, helps ensure low invasiveness to the patient 300. The sheath 40, with the above-mentioned inner diameter and wall thickness, permits insertion therein of therapeutic catheters and guiding catheters with larger outer diameters. Where the sheath 40 has a wall thickness of 0.08 to 0.14 mm, the above-mentioned effects become more conspicuous. The ratio of inner diameter to wall thickness, or (inner diameter)/(wall thickness), of the sheath 40 is in a range from 5 to 34, preferably from 8 to 27, more preferably from 8 to 20.

In addition, in the case of the introducer sheath 40 with a relatively small outer diameter, such as the above-mentioned "4 in 3," a diagnostic instrument and a therapeutic instrument can be introduced to the treatment part to be diagnosed and treated, by setting the introducer sheath 40 indwelling in the instep or the heel and utilizing the route including the posterior tibial artery 390, the fibular artery 400 or the anterior tibial artery 380 which has a small blood vessel diameter. The diameter of a blood vessel such as an artery is smaller as a given position is farther from the heart. In the case of performing diagnosis and treatment by setting an introducer sheath near the instep or heel where the posterior tibial artery 390, the fibular artery 400 or the anterior tibial artery 380 having a small blood vessel diameter extends, therefore, an introducer sheath 40 having a small outer diameter is needed.

Furthermore, each of the introducer sheaths 40 differing in size as above has the following effects.

Since the outer diameter of the introducer sheath 40 is reduced by 1 Fr size, an insertion scar after the percutaneous insertion of the introducer sheath 40 into a blood vessel or the like is comparatively small, and the stanching time can be shortened. In addition, invasiveness to vascular endothelium is relatively low, which helps ensure a lowered probability of blood vessel occlusion. Therefore, with the outer diameter of the introducer sheath 40 reduced by 1 Fr size, the period of time for which the patient 300 stays in a hospital is shortened, so that a physical burden on the patient 300 and an economic burden on the hospital can both be lessened. Furthermore, the occlusion of the patient's radial artery is reduced, whereby rehospitalization can be avoided.

In addition, for each of the introducer sheaths 40 differing in size as above, angiography catheters, intravascular ultrasound testing instruments and intravascular optical coherence tomography instruments can be applied or used as the diagnostic instrument. On the other hand, balloon catheters, drug-eluting balloon catheters, bare metal stents, drug-eluting stents, drug-eluting biodegradable stents, rotablators, thrombus suction catheters, or drug administration catheters can be applied or used as the therapeutic instrument. Further, guiding catheters and support catheters can be applied or used as the catheter. Thus, in using the introducer sheath 40, there are no specific restrictions as to the diagnostic instrument and the therapeutic instrument, so that versatility is secured.

For each of the introducer sheaths 40 differing in size as above, particularly in the TRI procedure, sharp bending of the sheath tube would rarely occur during the procedure. Even if sharp bending of the sheath tube should occur, plastic deformation upon the sharp bending would not easily occur, because of influences of material characteristics and the wall thickness. Therefore, the insertion resistance on the device to be inserted, such as a guiding catheter, is substantially the same as before the sharp bending of the sheath tube. In addition, a resistance value in this situation is not more than a sliding resistance value of the device inserted through the valve. Therefore, the insertion feeling for an operator is the same before and after the sharp bending of the sheath tube. Since the sheath 40 is less liable to suffer plastic deformation, a distal end of the device inserted can be prevented from being damaged, even when sharp bending of the sheath tube has occurred. The distal end of the instrument (device) to be inserted into a blood vessel is provided with a flexible tip for restraining damage to the blood vessel wall. Therefore, prevention of damage to the tip part leads to prevention of damage to the blood vessel wall.

As for the effects pertaining to both of the above-mentioned two kinds of introducer sheaths 40 differing in shape, the same or similar effects are produced also in the cases of the "5 in 4" and the "4 in 3."

While the one having the inner diameter that can be inserted a device having an outer diameter of 6 Fr size and the outer diameter that is equivalent to an outer diameter of a prior art introducer sheath corresponds to 5 Fr size, the one having the inner diameter that can be inserted a device having an outer diameter of 7 Fr size and the outer diameter that is equivalent to an outer diameter of a prior art introducer sheath corresponds to 6 Fr size, the one having the inner diameter that can be inserted a device having an outer diameter of 5 Fr size and the outer diameter that is equivalent to an outer diameter of a prior art introducer sheath corresponds to 4 Fr size, the one having the inner diameter that can be inserted a device having an outer diameter of 4 Fr size and the outer diameter that is equivalent to an outer diameter of a prior art introducer sheath corresponds to 3 Fr size have been described in this embodiment as above, these are mere examples, and other size may also be adopted. For example, the one may have the inner diameter that can be inserted a device having an outer diameter of 6 Fr size and the outer diameter that is equivalent to an outer diameter of a prior art introducer sheath corresponds to 5.5 Fr size. This example is so-called "half size".

The detailed description above describes features and aspects of embodiments, disclosed by way of example, of a method for diagnosis and treatment of an artery. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A method of treating comprising:
    inserting an introducer into a first blood vessel of a patient, the introducer comprising a dilator positioned inside a selected sheath which possesses open distal and proximal ends, the dilator comprising a distal end, the introducer being inserted into the first blood vessel while the distal end of the dilator extends distally beyond the distal end of the selected sheath, the selected sheath comprising an outer diameter substantially equal to an outer diameter of a first sheath and an inner diameter substantially equal to an inner diameter of a second sheath which has a Fr size that is one Fr size larger than a Fr size of the first sheath;
    drawing out the dilator from the first blood vessel and from the selected sheath while the selected sheath is kept indwelled in the first blood vessel;
    inserting a diagnostic instrument into the selected sheath that is indwelled in the first blood vessel, through the first blood-vessel and into a second blood vessel, the diagnostic instrument having an outer diameter inserted into the selected sheath that is smaller than a maximum outer diameter which can be inserted into and moved along the selected sheath;
    diagnosing, through use of the diagnostic instrument, whether a stenosis exists in the second blood vessel;
    drawing out the diagnostic instrument from the second blood vessel, the first blood vessel and the selected sheath;
    inserting a therapeutic instrument or a catheter permitting insertion of the therapeutic instrument, through the selected sheath that is indwelled in the first blood vessel so that the therapeutic instrument or the catheter is inserted through the first blood vessel and then into the second blood vessel, the therapeutic instrument or the catheter having the maximum outer diameter which is permitted to be inserted into the selected sheath and moved along the selected sheath, and when the catheter permitting insertion of the therapeutic instrument is inserted through the selected sheath and the first blood vessel and into the second blood vessel, the therapeutic instrument is inserted through the catheter and the first blood vessel and into the second blood vessel; and
    treating the stenosis in the second blood vessel through use of the therapeutic instrument, the first blood vessel being either a radial artery or a ulnar artery of the patient and the second blood vessel being a coronary artery of the patient.

2. The method according to claim 1, wherein the diagnostic instrument is an angiography catheter.

3. The method according to claim 1, wherein the therapeutic instrument is one of a balloon catheter, a drug-eluting balloon catheter, a bare metal stent, a drug-eluting stent, a drug-eluting biodegradable stent, an intravascular ultrasound testing instrument, a rotablator, a thrombus suction catheter, and a drug administration catheter.

4. A method of inserting an angiography catheter and a guiding catheter through a first artery into a second artery of a patient, the method comprising:
    preparing an introducer including a selected sheath and a dilator positioned in the selected sheath, the selected sheath comprising an outer diameter substantially equal to an outer diameter of a first sheath and an inner diameter substantially equal to an inner diameter of a second sheath which has a Fr size that is one Fr size larger than a Fr size of the first sheath, the dilator comprising an outer diameter substantially equal to an inner diameter of the selected sheath and being positioned in and movable along the selected sheath;
    inserting the introducer into the first artery while the dilator is positioned in the selected sheath;
    removing the dilator from the selected sheath while the selected sheath remains indwelled in the first artery;
    inserting the angiography catheter through the selected sheath and the first artery and into the second artery, the angiography catheter having an outer diameter equal to or smaller than a maximum outer diameter permitting insertion into and movement along the selected sheath;
    diagnosing, through use of the angiography catheter, whether or not the second artery is stenosed;
    removing the angiography catheter from the first and second arteries and from the selected sheath; and
    inserting the guiding catheter, having the maximum outer diameter permitting insertion into the selected sheath, through the selected sheath and the first artery and into the second artery, without replacing the sheath with another sheath having a size larger than the inner diameter of the selected sheath, the first artery being either a radial artery or a ulnar artery of the patient and the second artery being a coronary artery of the patient.

5. A method of inserting an angiography catheter and a guiding catheter through a first artery into a second artery of a patient, the method comprising:
preparing an introducer including a selected sheath and a dilator positioned in the selected sheath, the selected sheath comprising an outer diameter substantially equal to an outer diameter of a first sheath and an inner diameter substantially equal to an inner diameter of a second sheath which has a Fr size that is one Fr size larger than a Fr size of the first sheath, the dilator comprising an outer diameter substantially equal to an inner diameter of the selected sheath and being positioned in and movable along the selected sheath;
inserting the introducer into the first artery while the dilator is positioned in the selected sheath;
removing the dilator from the selected sheath while the selected sheath remains indwelled in the first artery;
inserting the angiography catheter through the selected sheath and the first artery and into the second artery, the angiography catheter having an outer diameter equal to or smaller than a maximum outer diameter permitting insertion into and movement along the selected sheath;
diagnosing, through use of the angiography catheter, whether or not the second artery is stenosed;
removing the angiography catheter from the first and second arteries and from the selected sheath; and
inserting the guiding catheter, having the maximum outer diameter permitting insertion into the selected sheath, through the selected sheath and the first artery and into the second artery, without replacing the sheath with another sheath having a size larger than the inner diameter of the selected sheath;
wherein the first artery is either a posterior tibial artery, a anterior tibial artery, or a popliteal artery of the patient and the second artery is a coronary artery of the patient.

* * * * *